United States Patent [19]

Gutman et al.

[11] 4,388,249

[45] Jun. 14, 1983

[54] 3-(ALKOXYPHENYLSULFONYL)A-CRYLONITRILES

[75] Inventors: Arnold D. Gutman, Berkeley; John W. Williams, Vallejo, both of Calif.

[73] Assignee: Stauffer Chemical Company, Richmond, Calif.

[21] Appl. No.: 352,679

[22] Filed: Feb. 26, 1982

Related U.S. Application Data

[63] Continuation of Ser. No. 221,119, Dec. 29, 1980, Pat. No. 4,331,480.

[51] Int. Cl.³ .............................................. C07C 121/75
[52] U.S. Cl. ................................................. 260/465 F
[58] Field of Search ......................................... 260/465 F

[56] References Cited

U.S. PATENT DOCUMENTS 3,159,532 12/1964 Heininger et al. ......... 260/465 G X
3,159,666 12/1964 Heininger et al. ............. 260/465 G
3,541,119 11/1970 Richter et al. ............. 260/465 K X
4,079,148 3/1978 Oeckl et al. .......................... 424/304

Primary Examiner—Dolph H. Torrence
Attorney, Agent, or Firm—Joel G. Ackerman

[57] ABSTRACT

Compounds having the formula

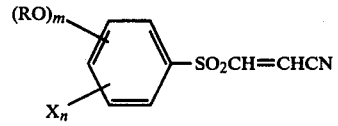

in which R is lower alkyl; X is halogen or lower alkyl; m is 1 or 2; and n is 0, 1, 2 or 3, are effective biocides or biostats for protection of plastic or polymeric materials against attack by microorganisms, and for controlling or inhibiting the growth of algae.

2 Claims, No Drawings

3-(ALKOXYPHENYLSULFONYL)ACRYLONITRILES

This is a continuation of application Ser. No. 221,119, filed Dec. 29, 1980, now U.S. Pat. No. 4,331,480.

BACKGROUND AND PRIOR ART

This invention relates to a series of novel compounds which have been found useful as microbiocides in controlling bacteria, fungi, actinomycetes and algae. These compounds, as will be seen from the data below, have particular utility as general algicides and biocides, particularly for the protection of plastics and polymeric materials against attack by microorganisms.

The invention also relates to methods of controlling algae, bacteria, fungi and actinomycetes, and for protecting plastic or polymeric compositions from attack by microorganisms by the use of an algicidally or microbiocidally effective amount of such novel compounds, and to compositions containing such effective amounts of such compounds.

Synthetic, film-forming materials such as those used in the manufacture of plastic or polymeric films, and various types of plastics or polymers, are known to be subject to attack by microorganisms. Such microorganisms include bacteria, fungi and actinomycetes. The last mentioned are microorganisms found in soil which contain no chlorophyll. They are usually classified with the bacteria, but resemble both bacteria and fungi; they are intermediate in size between fungi and bacteria.

Such microorganisms attack plastics and polymers and can cause damage or deterioration ranging from discoloration and staining to embrittlement or actual disintegration, depending on the type of plastic or polymer, and the environment in which it is situated. Severe damage can be produced to plastics or polymers which are utilized in certain environments, such as those with high humidity. Plastics and polymers are commonly used for instance, in underground construction, in pipes and conduits, cables, sheathing, insulation, etc. In such an environment, they are subject to severe deterioration by soilborne microorganisms. Similarly, plastics and polymers used in materials such as swimming pool liners, awnings, camping equipment, and other articles for outdoor use, and in upholstery, car tops, shoes, boots and clothing, in which they may be exposed to natural humidity and/or sweat, possibly in combination with somewhat elevated temperatures, are subject to microbial deterioration.

In addition to physical deterioration of plastics and polymers, microorganisms growing on the surface of such materials can cause discoloration and/or staining thereof resulting in a shortening of the useful life of said materials for at least aesthetic purposes. Actinomycetes, in particular, growing on the surfaces of plastics and polymers can produce colored byproduct dyes which are soluble in the plasticizers used in such substances, and which migrate through the substance via the plasticizer, resulting in the phenomenon known as "pink staining." In addition, surface growth of microrganisms on polymers may interfere with functional performance, for instance when used as lubricating surfaces.

In order to prevent attack and deterioration or discoloration of polymeric or plastic materials by microorganisms, a number of compounds have been used as industrial biocides.

For use as a biocide in connection with plastics and polymers, a compound must have the following properties:

effectiveness at low levels against many microorganisms; compatibility with plasticizers and other chemicals used in the formulation of plastic and polymeric products;
lack of a disadvantageous color or odor;
resistance to leaching from plastic or polymeric materials; and particularly;
  (a) thermal stability at temperatures over 300° F. (148° C.) so that deterioration of the biocide does not occur during the processing of plastics and polymers;
  (b) mobility—the ability to migrate through the plastic, polymer or plasticizer utilized therein, so as to be dissipated therethrough; and
  (c) stability towards ultraviolet and other light radiation.

Such properties are necessary for plastics and polymers which are cast, rolled, molded, extruded or otherwise fabricated into a continuous form, for use in various ways such as raw materials for the manufacture of plastic or polymer articles or as plastic or polymeric coatings, as well as plastics and polymers which are knitted or woven into continuous fibers.

Both the prevention of growth in the contact area, that is on the material itself, and inhibition of growth in a zone surrounding the contact area, are of importance in order to prevent the spread of an actively growing organism. The biocide must possess a positive antimicrobial activity in a zone of inhibition surrounding the article; otherwise, a compound which is effective as a biocide in the contact area itself would nevertheless not control heavy growth on the surface or on substances associated with or attached to the material. Such property is important, for instance, for fabrics in which a polymeric fiber, such as a polyester or polyamide, is laminated to a cotton or other cellulosic backing such as canvas.

Many of the industrial biocides currently used in connection with plastics, polymers and cellulosic fibers are organometallics. These compounds are effective in preventing microbial attack on such materials. However, such compounds may be suspect for reasons of toxicity or environmental effect and problems caused by their handling and are now less accepted in some of the industrial uses in which they have hitherto been employed. It has thus become desirable to find new, nonmetallic biocides for use with such materials.

SUMMARY OF THE INVENTION

The novel compounds which have been found to possess the activity of controlling microorganisms, particularly in plastics and polymers, and controlling algae, have the formula

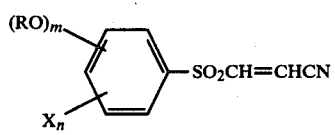

in which R is lower alkyl; X is halogen or lower alkyl; m is 1 or 2; and n is 0, 1, 2 or 3.

The term "lower alkyl" is meant to include such groups having from 1 to 6, preferably from 1 to 4, carbon atoms, such as methyl, ethyl, and the various propyl, butyl, amyl and hexyl moieties. The term "halogen" includes chloro, bromo, fluoro, and iodo, and is preferably chloro.

In a preferred embodiment, R is $C_1$-$C_4$ alkyl (most preferably methyl), m is 1 and n is 0.

This invention also encompasses a method for protecting a plastic or a film-forming polymer composition which is fabricated into a continuous form, against attack by bacteria, fungi or actinomycetes comprising incorporating into said composition or continuous form, or coating the same with, a microbiocidally effective amount of a compound as above defined. It further encompasses such plastic or film-forming compositions containing, or coated with, a microbiocidally effective amount of such compound.

This invention also encompasses a method of controlling or inhibiting the growth of algae, comprising applying to the algae or to a locus where control or inhibition is desired, an algicidally effective amount of such compound.

The invention further encompasses microbiocidal or algicidal compositions for use in the above-mentioned methods which comprise a microbiocidally or algicidally effective amount, respectively, of such compound.

The term "film-forming" is meant to refer to polymeric particles, whether present as dry particulate matter, or in liquid, dissolved, suspended, continuous, or any other form, particularly including the ultimate form for which such particles are designed. The term "plastic" is similarly intended to be regarded as a broad term and is to be understood to include polymeric materials which can be cast, extruded, injection molded, or compression molded into a desired state.

Certain polymers such as alkyd resins, polyester based urethanes, polyesters, and certain cellulosic polymers such as benzyl-, methyl-, hydroxyethyl-, and sodium carboxymethyl-cellulose, are susceptible in and of themselves to attack by microorganisms. Other polymers such as polyethylene and polystyrene may become susceptible after degradation through prolonged weathering. Still other plastics and polymers, such as polyvinyl chloride, are considered in and of themselves to be generally resistant to such attack. However, many substances utilized with polymers to produce polymeric or plastic products, for instance, flexible polyvinyl chloride sheeting, contain additives such as plasticizers, stabilizers, fillers, lubricants, thickening agents or starch sizings for synthetic fibers, which are susceptible to attack by microorganisms. Thus, plastics or other materials formulated from a polymer resistant to such attack but incorporating a substance such as a plasticizer, which is susceptible to such attack, are thereby rendered susceptible to deterioration, discoloration, and other damage from microorganisms. Alternatively, microorganisms can grow on debris, lubricants, or other materials adhering to the surface of a non-susceptible plastic or polymer. Metabolic products of such organisms may cause etching of the substrate material.

The compounds to which the present invention relates have been found to possess the necessary high thermal stability, the necessary unexpected ability to migrate through plastics, and the requisite, surprisingly high stability to ultraviolet radiation.

The compounds of this invention may be prepared according to several processes.

In one process, a sulfonyl chloride is reacted with acrylonitrile to produce a sulfonyl haloacetonitrile which is then dehydrochlorinated to produce the desired product (see, for instance, U.S. Pat. No. 3,159,666):

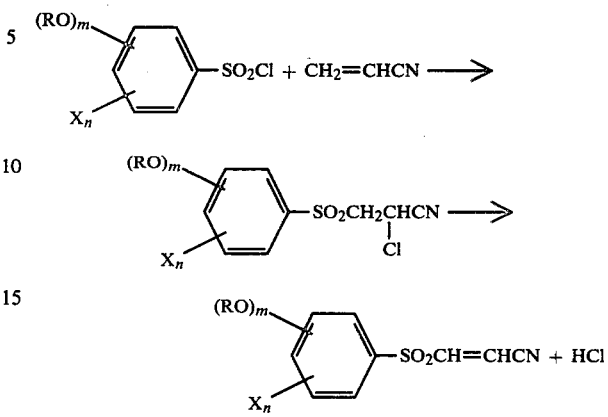

In another process, a sulfonyl chloride is reacted with acrylonitrile in the presence of cupric chloride, an alkaline earth metal oxide and a heterocyclic amine base, in a single step:

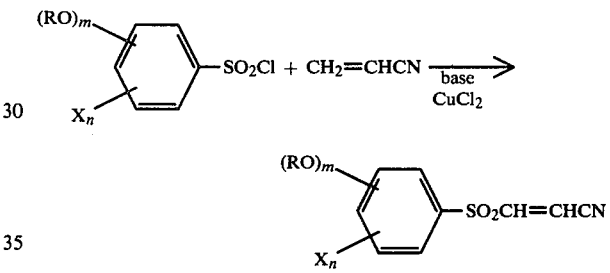

Such a process is more completely described in U.S. patent application Ser. No. 222,203, filed Jan. 2, 1981, of James M. Photis, entitled "Process for the Preparation of Unsaturated Sulfones", commonly assigned.

The sulfonyl chlorides can be prepared, if necessary, by alkylation of the appropriate phenol.

In a third process, an alkali metal (preferably sodium) salt of a sulfinic acid is reacted with 2-chloroacrylonitrile:

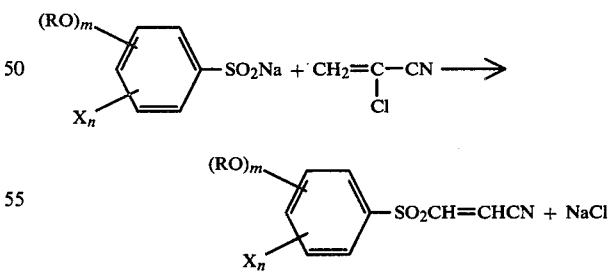

This reaction is generally conducted in aqueous media in the presence of buffers such as sodium acetate and boric acid, at approximately room temperature.

EXAMPLE 1

Preparation of 3-(4-methoxyphenylsulfonyl)acrylonitrile

In a flask, 59.5 g. (0.31 mole) sodium 4-methoxybenzenesulfinate, 25.4 g. (0.31 mole) sodium acetate and 19.2 g. (0.31 mole) boric acid were dissolved in a mixture of 150 ml. water and 275 ml. isopropyl alcohol. There was then added, with stirring, dropwise, 33.9 g. (31 ml., 0.39 mole) 2-chloroacrylonitrile. The mixture was stirred for some time at room temperature. Water was then added and the mixture stirred for one hour. A precipitate formed, which was filtered, washed with water and ethanol, and dried.

The structure of the compound, which had a melting point of 120°-122° C., was confirmed by infrared, nuclear magnetic resonance, and mass spectroscopy.

Evaluation

The compound of Example 1 was tested for microbiocidal and algicidal activity as follows:

Anti-microbial Screening tests with ultraviolet and weather exposure (plastics/polymers)

Dry blends of polyvinyl chloride were prepared by dry mixing the following ingredients (by weight): 100 parts Dia 450 polyvinyl chloride resin (Diamond Shamrock Chemical Corporation), 40 parts dioctyl phthalate plasticizer, 3.50 parts Mark KCB cadmium-barium-zinc heat stabilizer/lubricant, 1.50 parts Mark C organic phosphite heat stabilizer/lubricant (Mark Chemicals available from Argus Chemical Division, Witco Chemical Company) and 0.25 parts stearic acid. To one set of blends there was additionally included one (1) part Mark 202A benzophenone ultraviolet light stabilizer. The other set of blends was not stabilized against ultraviolet radiation.

The blends were then fluxed on hot rollers at 320° F. (160° C.) until homogeneously blended. Sufficient quantities of the compound prepared in Example 1 above was added, to provide polymers containing 0.5 to 1.0 weight % of the test compound (based on the polymer). The polymers were further milled for ten minutes at the same temperature, then sheeted off as a film.

Samples of the films were submitted to 100 and 300 hours of exposure treatment in a xenon-type weatherometer (weather-simulating exposure test apparatus) programmed for continuous light with 18 minutes of water spray every two hours. The exposure was conducted according to ASTM Standard G 26-70.

Unexposed film, and film which had been exposed to the weather simulation for 100 and 300 hours, respectively, were tested for anti-microbial activity as follows:

(a) Samples of film which had been unexposed, exposed for 100 hours, and exposed for 300 hours were placed on samples of nutrient agar variously inoculated with bacteria, actinomycetes or fungi. The organisms were:

BACTERIA

*Staphylococcus aureus* ATCC 6538 (gram-positive)
*Klebsiella pneumoniae* ATCC 4352

ACTINOMYCETES

*Stv. reticulum* ATCC 25607 (pink staining organism)

FUNGI: a mixed fungal spore suspension of

*Aspergillus niger* ATCC 9642
*Aspergillus flavus* ATCC 9643
*Penicillium funiculosum* ATCC 9644
*Chaetomium globosum* ATCC 6205.

The samples inoculated with bacteria or actinomycetes were incubated for 24 hours at 37° C.; those containing fungi were incubated for 14 days at 28° C. After incubation, anti-microbial activity was evaluated by measuring the size of a clear zone of no growth (i.e., zone of inhibition) around each sample and visually rating the degree of growth or stain on the sample.

(b) A second series of fungicidal tests was conducted using similar samples placed on agar containing non-nutrient mineral salts and inoculated with a mixed fungi spore suspension of: *Aspergillus niger*, ATCC 9642, *Penicillin funiculosum*, ATCC 9644, *Chaetomium globosum*, ATCC 6205, *Aureobasidium pullulans*, ATCC 9348, and *Trichoderma sp.*, ATCC 9645. The samples were incubated for 21 days at 28° C. (ASTM Standard method G. 21-75). Antifungal activity was evaluated by visually rating the degree of fungal growth on the samples.

The results of these tests are contained in the following Table I.

TABLE I

| Example 1 wt. % | Stabilized | Exposure, hrs. | Zone of Inhibition, mm/growth or staining | | | | |
|---|---|---|---|---|---|---|---|
| | | | Staph. aureus | K. pneum. | Stv. ret. | Mixed fungi (a) | Mixed fungi (b) |
| 0.5 | + | 0 | 12/N | 6/N | 12/NS | 0/N | N |
| 0.5 | + | 100 | 11/N | 5.5/N | 10/NS | 0/N | N |
| 0.5 | + | 300 | 8/N | 2/N | 5/NS | 0/N | N |
| 0.5 | − | 0 | 12/N | 6/N | 12/NS | 0/N | N |
| 0.5 | − | 100 | 10/N | 4.5/N | 9/NS | 0/T | N |
| 0.5 | − | 300 | 9/N | 2/N | 7/NS | 0/T | N |
| 1.0 | + | 0 | 12/N | 8.5/N | 13/NS | 2/N | N |
| 1.0 | + | 100 | 14/N | 8.5/N | 12/NS | 2/N | N |
| 1.0 | + | 300 | 9/N | 5/N | 7/NS | 1/N | N |
| 1.0 | − | 0 | 14/N | 8/N | 12/NS | 2/N | N |
| 1.0 | − | 100 | 12/N | 7/N | 9/NS | 1/N | N |
| 1.0 | − | 300 | 11/N | 4/N | 8/NS | 1/N | N |
| Control | + | 0 | 0/G | 0/G | 0/NS | 0/HG | HG |
| | + | 100 | 0/G | 0/G | 0/NS | 0/HG | HG |
| | + | 300 | 0/G | 0/G | 0/NS | 0/HG | HG |
| | − | 0 | 0/G | 0/G | 0/NS | 0/HG | HG |
| | − | 100 | 0/G | 0/G | 0/NS | 0/HG | HG |

TABLE I-continued

| Example 1 wt. % | Stabilized | Exposure, hrs. | Zone of Inhibition, mm/growth or staining | | | | |
|---|---|---|---|---|---|---|---|
| | | | Staph. aureus | K. pneum. | Stv. ret. | Mixed fungi (a) | Mixed fungi (b) |
| | − | 300 | 0/G | 0/G | 0/TS | 0/HG | HG |

Key N — No growth in contact area
T — Trace growth in contact area (less than 10%)
G — Moderate growth in contact area (30–60%)
HG — Heavy growth in contact are (greater than 60%)
NS — No staining in contact area
TS — Trace of staining in contact area
+ — U.V. stabilizer included
− — no U.V. stabilizer It should be noted that the activity of the compound was not substantially affected by ultraviolet radiation, as shown by its performance in the absence of an ultraviolet stabilizer in the formulation. Such stability towards ultraviolet radiation would not have been expected from the structure of this compound; it contains an activated double bond, which would be expected to be oxidized in the presence of ultraviolet light and air.

Algicidal Screening Test

The test organism was *Chlorella pyrenoidosa*.

A broth of the organism was prepared, sterilized and inoculated with stock Chlorella culture, and allowed to develop in the presence of sunlight for 5 days.

Test tubes were loaded with 4.2 ml. of the broth and sterilized. An acetone solution of the compound of Example 1 was prepared, and aliquots were added to the test tubes to provide concentrations of the test compound in the broth of 1, 5, 10 and 50 ppm. The test tubes were placed in a rack next to a window and rotated 180° C. twice each week.

Observations of the tubes were performed after 1, 2, and 3 weeks. The growth of algae was determined by the size of the plug (if any) at the bottom of the tube, on a scale of 0–4, with 0 indicating no growth, 1 indicating about 4 mm. size plug, and 4 indicating a plug of 7 mm. or larger. The results of this test are shown in the following Table II.

TABLE II

| Concentration ppm | Algal Growth Rating | | |
|---|---|---|---|
| | 1 week | 2 weeks | 3 weeks |
| 1 | 2+ | 3+ | 3+ |
| 5 | 0 | 0 | 0 |
| 10 | 0 | 0 | 0 |
| 50 | 0 | 0 | 0 |

The minimum inhibitory concentration (M.I.C.) of the test compound was determined to be less than 5 ppm.

Methods of Formulations

For use as plastics or polymer biocides, the compounds disclosed herein may be incorporated in plastics or films or products made therefrom, in an amount ranging from 0.001 to 2.0% by weight of the total composition, preferably 0.01 to 1.0, and most preferably 0.01 to 0.5%, by weight. The incorporation may be performed, as was done in the examples, by incorporating an amount of the biocide in a dry mix which is then processed to produce the desired plastic or polymer or ultimate product containing it. Alternatively, the biocide may be incorporated in a dry blend at a higher rate, for instance, 12–13% by weight, to which a small amount of an extrusion aid (for instance barium-calcium stearate) is added, and the blend extruded to form a rod, from which pellets are cut, as described for instance in U.S. Pat. No. 4,086,297. The pellets can then be utilized as a means to incorporate the biocide into subsequent plastic or polymer formulations, with the number of pellets added being determined so as to produce an overall polymer composition including the biocide in the desired or appropriate amount.

More commonly, the antimicrobial compound is predissolved or dispersed in a liquid carrier solvent such as a plasticizer for a polymeric resin, thereby providing a vehicle for the biocide for ease of incorporation and to promote its migration throughout the resin, particularly to its surface. Usually, the biocide is dissolved in a first solvent and then diluted with the desired resin-compatible plasticizer second solvent to provide a final liquid solution wherein the first solvent acts as a coupling solvent for the biocide and plasticizer to maintain homogeneity. Both first and second solvents are themselves mutually compatible with each other and the polymeric resin system. See, for instance, U.S. Pat. No. 3,288,674.

For use in controlling or inhibiting the growth of algae, the active compounds, per se or in a formulation with inert carriers or diluents and optionally other substances, are introduced into an aqueous environment in which algae are present, or may occur. The manner in which the aqueous environment is treated will vary with the specific problems encountered. The compound may be utilized for instance, in ponds, lakes and other areas in which water, particularly industrial process water or effluents, is stored. Water flowing sites such as drainage ditches may be similarly treated. The compound may be utilized for the control of algae in industrial cooling towers and other water recirculating systems.

When so used, the compounds are added to the aqueous environment in an algicidally effective amount, which usually ranges from about 0.1 to about 50 ppm, preferably from about 0.1 to about 10 ppm.

Examples of algicidal formulations in which the active compounds may be employed are dispersable or soluble powders or solids, or emulsifiable concentrates. Suitable carriers or diluents for use in preparation of such formulations include solvents, such as aromatic hydrocarbons (optionally chlorinated) for instance, xylene, benzene and chlorobenzenes, paraffins such as petroleum fractions, alcohols, for instance methanol or ethanol, and amines such as ethanolamine or dimethylformamide; finely divided solid carriers, for instance, natural and synthetic meals or powders including kaolin, alumina, chalk, talc, or highly dispersed silicates, emulsifiers including nonionic and anionic emulsifiers such as polyoxyethylene fatty acid esters, polyoxyethylene fatty alcohol ethers, alkyl or aryl sulfonates, or magnesium stearate or sodium oleate; and dispersing agents such as lignin, methyl cellulose, or sulfite waste liquors. Solid pellets or large tables containing the active compounds may be manufactured by mixing a dispersible or solid powder formulation of said compounds with a binder.

Emulsions employing the algicidal compounds disclosed herein may be prepared by dissolving the active compounds in a waterimmiscible solvent such as aromatic hydrocarbons, petroleum fractions, and the like, in asociation with a surfactant such as mentioned above, to obtain an emulsifiable concentrate which is then poured into water, preferably with vigorous agitation. Emulsions may also be prepared by dissolving the active compounds in a water-miscible solvent such as Carbitol (diethylene glycol monoethyl ether) or an analog of Carbitol, acetone, a lower alkanol, Cellosolve (ethylene glycol monoethyl ether), and the like to obtain a concentrate which can then be added to water containing a surfactant such as mentioned above, preferably with vigorous agitation.

In addition to the active compounds, algicidal formulations according to this invention may also contain other active ingredients suitable for control of algae, or for other uses such as control of aquatic weeds or other organisms which may be found in the environment to be treated.

What is claimed is:

1. A compound having the formula

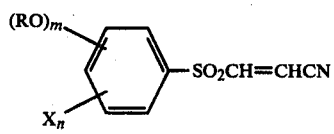

in which R is lower alkyl; X is halogen or lower alkyl; m is 1 or 2; and n is 1, 2, or 3.

2. A compound according to claim 1 in which R is $C_1$–$C_4$ alkyl.

* * * * *